United States Patent

Tenti

[11] Patent Number: 6,126,441
[45] Date of Patent: Oct. 3, 2000

[54] BUCCAL TUBE

[76] Inventor: Federico Vincenzo Tenti, Via Podgora 3, 16145 Genoa, Italy

[21] Appl. No.: 09/179,134

[22] Filed: Oct. 26, 1998

[30] Foreign Application Priority Data

Oct. 29, 1997 [IT] Italy ..................................... FI97A240

[51] Int. Cl.[7] ..................................... A61C 3/00
[52] U.S. Cl. ..................................... 433/17
[58] Field of Search ..................................... 433/17, 9, 3

[56] References Cited

U.S. PATENT DOCUMENTS

| | | | |
|---|---|---|---|
| 3,302,288 | 2/1967 | Tepper | 433/17 |
| 3,815,238 | 6/1974 | Wallshein | 433/17 |
| 4,322,206 | 3/1982 | Reynolds | 433/17 |
| 4,487,580 | 12/1984 | Ridgeway | 433/3 |
| 5,203,804 | 4/1993 | Nikutowski et al. | 433/17 |

*Primary Examiner*—John J. Wilson
*Attorney, Agent, or Firm*—McGlew & Tuttle, P.C.

[57] ABSTRACT

Buccal tube consisting of a body (1) with a base section (2) which is to be attached to a tooth face, and of at least two tubular elements providing seats for corresponding archwires, which features a groove (5) on the vestibular side into which orthodontic instruments can be introduced to position the base section (2) on the corresponding tooth.

9 Claims, 2 Drawing Sheets

BUCCAL TUBE

FIELD OF THE INVENTION

BACKGROUND OF THE INVENTION

The present invention relates to a buccal tube, particularly of the double type for molars.

Buccal tubes for molars are used for housing the final sections of orthodontic archwires associated with numerous orthodontic aids corresponding to each tooth, in order to exert strength on the teeth themselves, the entity and direction of this strength depending on the therapeutical treatment. Said buccal tubes are fixed directly on the teeth with adhesive means or orthodontic bands consisting of metallic bands surrounding each tooth, to which buccal tubes are welded. When positioning said tubes, it can be rather difficult to orientate them in relation to each tooth and to the orthodontic archiwire which is to be supported.

SUMMARY AND OBJECTS OF THE INVENTION

The main aim of the present invention is to overcome the above mentioned inconveniences.

This result has been obtained by building a buccal tube having the features described in a body including a base section attachable to a tooth face. The body includes a tubular element for receiving arch wires. The body also defines a groove positioned diametrically opposite the base section, where the groove has a shape for receiving and temporarily affixing the body to a dental tool for positioning the buccal tube onto the tooth face. The body preferably includes two diametrically opposite, substantially parallel, and substantially flat grasping surfaces which are positioned on gingival and occlusal sides of the body. The grasping surfaces are shaped for grasping by forceps in order to position the buccal tube onto the tooth face.

A first advantage of the present invention is related to the correct positioning of the buccal tube. Another advantage is derived from the structure of occlusal and gingival buccal tube surfaces which can be parallel with each other, so that they can be easily grasped with dental forceps, for instance with dental forceps commonly used for orthodontic aids. A further advantage is related to the tubular elements features by the buccal tube which may present an oblique cut at their ends i.e. they may end in oblique convex edges. Thanks to the structure described, patients can easily bear the buccal tubes once they are positioned inside their mouths owing to the absence of sharp edges, placed toward the vestibule and, at the same time, the introduction of orthodontic archwires into the tubular elements becomes easier.

Technicians operating in this field will better understand why this invention is so advantageous and what its techincals features are by examining the enclosed drawings as an embodiment of this invention which should not be considered a limitation wherein.

DESCRIPTION OF THE PREFERRED EMBODIMENT

Figure 1:
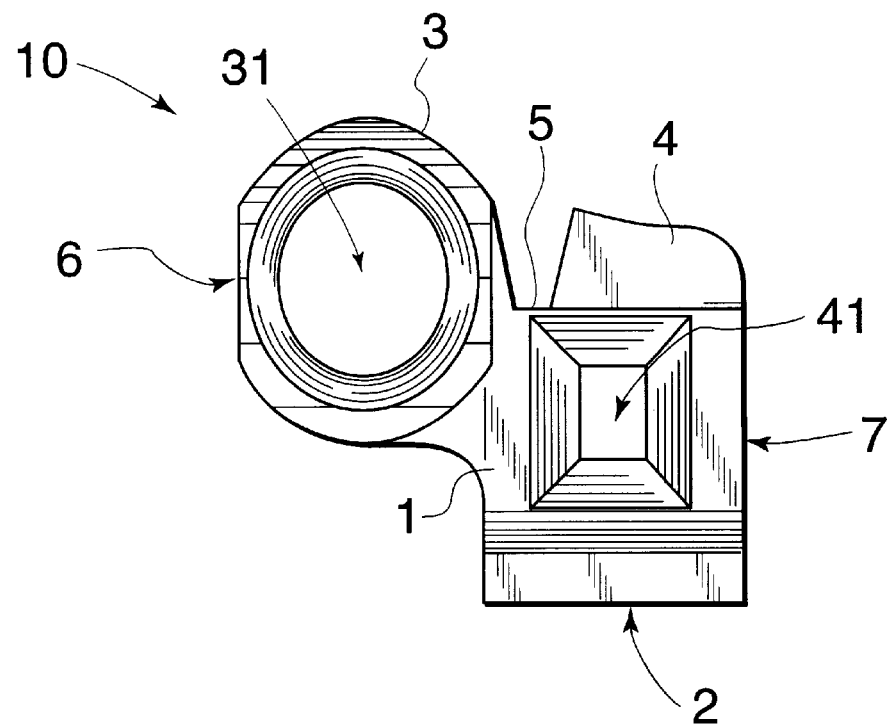
FIGS. 1 and 2 show a front view and, respectively, a plan view of the present buccal tube.
Figure 2:
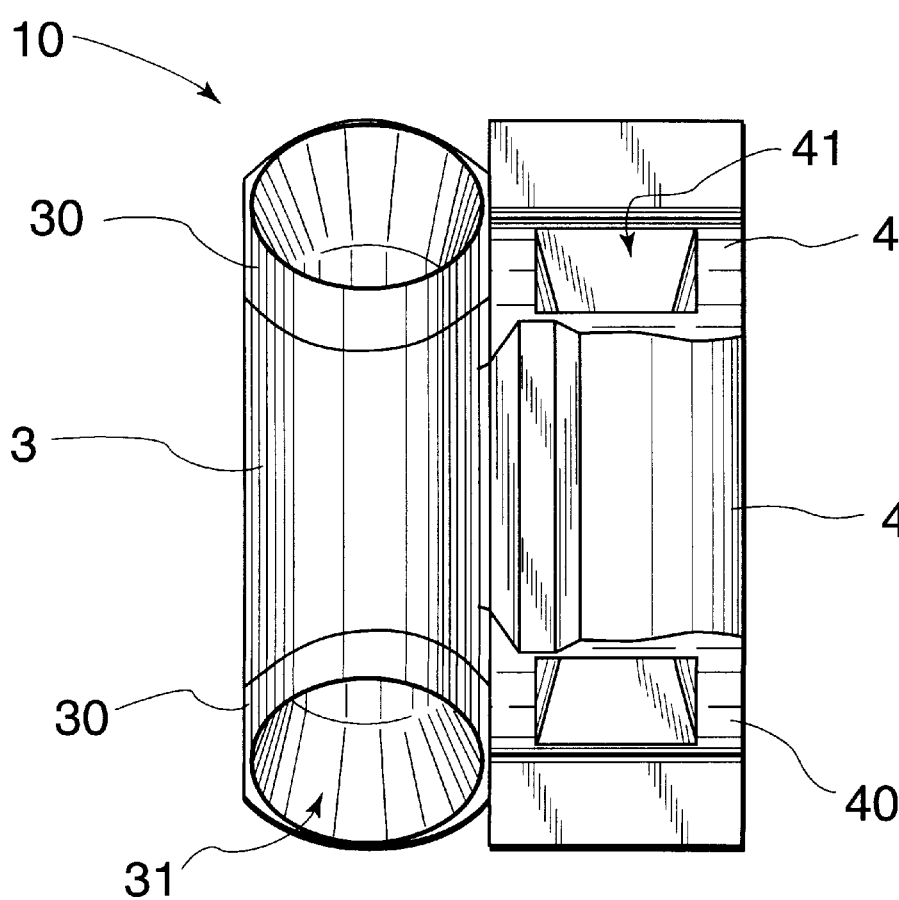
Figure 3:
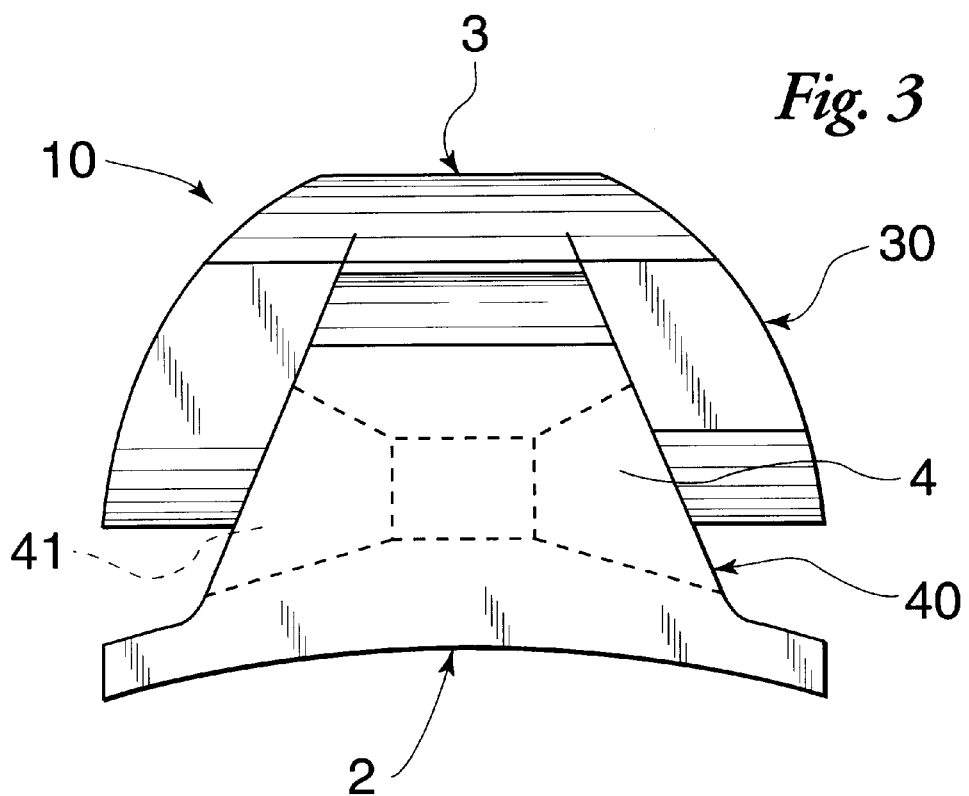
FIGS. 3 and 4 are side views of the above mentioned buccal tube.
Figure 4:
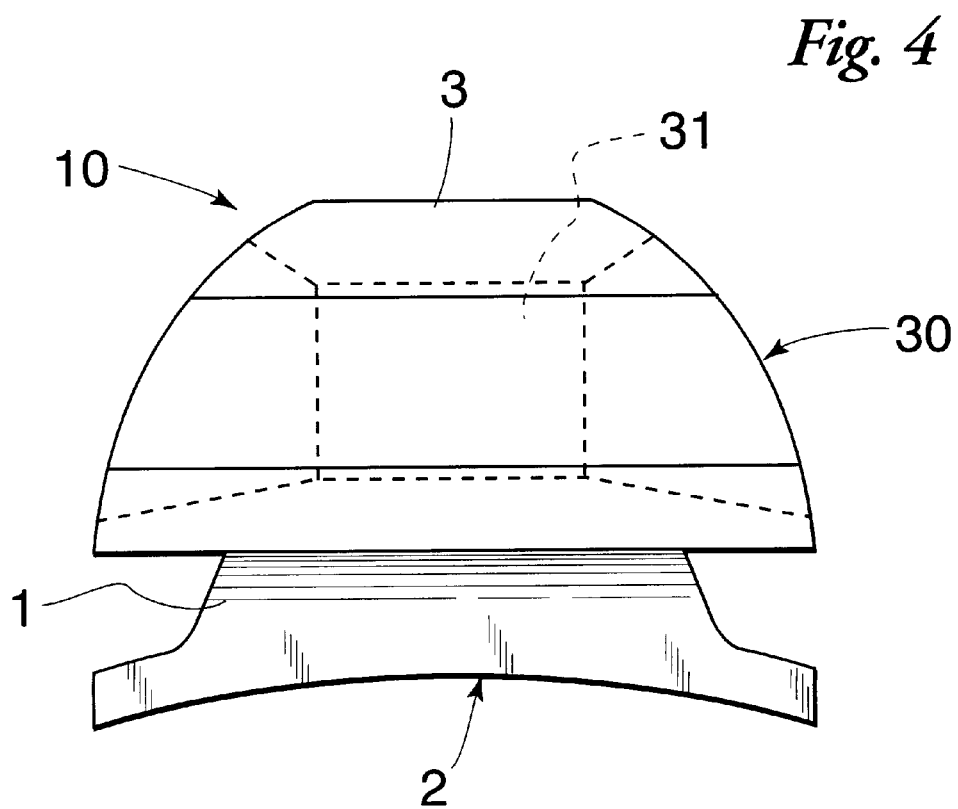

In the enclosed figures (10) indicates an embodiment of the buccal tube in its entirety. The buccal tube (10) consists of a body (1) which can be built according to a technique called "metal injection moulding". The body of the buccal tube features a base section (2) which is to be attached to each tooth face, usually the vestibular side. For this reason, said base section may feature a curved surface according to the corresponding tooth face section. The body (1) is also provided with two tubular elements (3, 4) providing seats for the corresponding archwires, which are not shown in the drawings. Particularly, the tubular element (3) features a hole (31) with a circular section for a corresponding section wire.

Similarly, the tubular element (4) features an opening (41), having quadrilateral rectangular section, which provides a seat for a corresponding archwire.

Advantageously, the buccal tube (10) subject of the present invention features a groove (5) on the vestibular side, i.e. on the opposite edge of the base section (2).

This groove (5), which in the illustrated example is placed between the two tubular elements (3, 4) and parallel with them, facilitates the placement of the buccal tube (10). In fact the end of an instrument (which is not shown in the enclosed drawings and which can act as a screwdriver and can be manipulated by orthodontists) may be inserted into said groove (5) to facilitate the orientation of the buccal tube (10).

A further characteristic of the buccal tube (10) subject of this invention is related to the free ends (30, 40) of the tubular elements (3, 4); in fact, such ends (30, 40) are bevelled and oblique, in particular they are convex. On one hand, this facilitates the introduction of the corresponding archwire into the seats (31, 41) and, on the other hand, since the buccal tube is not in direct contact with the inner part of patients' cheecks, it can be easily borne by patients themselves.

In addition, the buccal tube (10) may feature two opposite even and flat grasping sufaces (6, 7) placed on the gingival and occlusal edge respectively, which are parallel with each other. As a consequence, the buccal tube (10) can be easily grasped by means of dental forceps.

In practice, details in the execution may equally vary as regards shape, size, placement of the elements, kind of material used, but they are in agreement with the solution adopted within the limits of the safety offered by the present patent.

I claim:

1. A buccal tube comprising:
   a body including a base section attachable to a tooth face, said body including two tubular elements forming seats for receiving archwires, said body defining a groove on a vestibular side of said body and positioned diametrically opposite said base section, said groove having a shape for receiving a dental tool.

2. The buccal tube in accordance with claim 1, wherein: said groove is substantially parallel with said two tubular elements.

3. The buccal tube in accordance with claim 2, wherein: said groove is positioned between said two tubular elements.

4. The buccal tube in accordance with claim 1, wherein: said groove is positioned between said two tubular elements.

5. The buccal tube in accordance with claim 1, wherein: said tubular elements include beveled oblique ends.

6. The buccal tube in accordance with claim 5, wherein:

said ends are convex.

7. The buccal tube in accordance with claim 1, wherein:

said body includes two opposite parallel even surfaces positioned on gingival and occlusal edges of said body respectively.

8. The buccal tube in accordance with claim 1, wherein:

said body includes two diametrically opposite, substantially parallel, substantially flat grasping surfaces positioned on gingival and occlusal sides of said body, said grasping surfaces being shaped for grasping by forceps to position the buccal tube onto the tooth face.

9. A buccal tube comprising:

a body including a base section attachable to a tooth face, said body including a tubular element for receiving archwires, said body defining a groove positioned diametrically opposite said base section, said groove having a shape for receiving and temporarily affixing said body to a dental tool for positioning of the buccal tube onto the tooth face;

said body includes two diametrically opposite, substantially parallel, substantially flat grasping surfaces positioned on gingival and occlusal sides of said body, said grasping surfaces being shaped for grasping by forceps to position the buccal tube onto the tooth face.

* * * * *